(12) United States Patent
Dhawale et al.

(10) Patent No.: US 6,879,660 B2
(45) Date of Patent: Apr. 12, 2005

(54) METHOD AND APPARATUS FOR REDUCING SPECTRALLY-SENSITIVE ARTIFACTS

(75) Inventors: Paritosh Jayant Dhawale, Brookfield, WI (US); Douglas Albagli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 100 days.

(21) Appl. No.: 10/323,801

(22) Filed: Dec. 18, 2002

(65) Prior Publication Data

US 2004/0120468 A1 Jun. 24, 2004

(51) Int. Cl.$^7$ ............................................... H05G 1/64
(52) U.S. Cl. ........................................................ 378/98.8
(58) Field of Search .................... 378/19, 98.8, 207; 250/252.1

(56) References Cited

U.S. PATENT DOCUMENTS

| | | | |
|---|---|---|---|
| 3,848,130 A | * 11/1974 | Macovski | 378/98.9 |
| 4,789,930 A | * 12/1988 | Sones et al. | 378/207 |
| 6,266,391 B1 | 7/2001 | Albagli | 378/98.2 |
| 6,314,160 B1 | 11/2001 | Dhawale et al. | 378/98.2 |
| 6,393,098 B1 | 5/2002 | Albagli | 378/98.2 |
| 6,414,315 B1 | 7/2002 | Wei et al. | 250/370.11 |

* cited by examiner

Primary Examiner—Craig E. Church
Assistant Examiner—Jurie Yun
(74) Attorney, Agent, or Firm—Fletcher Yoder (57) ABSTRACT

A technique is provided in which a gain correction map derived for a detector at one X-ray spectrum may be adapted to accommodate images acquired by the detector at a different X-ray spectrum. The technique accounts for the physical variations in the detector which may produce spectrally-sensitive artifacts as well as for the particular image acquisition conditions. A technique is also provided for correcting edge artifacts in an acquired image by measuring median signal intensity within columns or rows of the image and deriving correction factors for the respective edge columns or rows based upon the trends of the median signal intensities. A technique is also provided for storing detector attributes during a manufacturing calibration process and accessing them during system operation such that a suitable gain correction factor is employed based upon the spectrum and operating conditions.

34 Claims, 5 Drawing Sheets

METHOD AND APPARATUS FOR REDUCING SPECTRALLY-SENSITIVE ARTIFACTS

BACKGROUND OF THE INVENTION

The present invention relates generally to a technique medical imaging and in particular to the field of digital X-ray. In digital X-ray imaging, two correction steps may be performed on raw images, namely offset correction and gain calibration. The gain calibration compensates for gain non-uniformities in the digital detector which may be present in an offset corrected raw image using a gain calibration map. Specifically, the present invention relates to a process for adapting a gain calibration map in an X-ray image to reduce or eliminate artifacts, particularly those visible in the display of a flat object.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector. The surface of the detector converts the radiation to light photons which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

Digital X-ray imaging systems are particularly useful due to their ability to collect digital data which can be reconstructed into the images required by radiologists and diagnosing physicians, and stored digitally or archived until needed. The digital data produced by direct digital X-ray systems can be processed and enhanced, stored, transmitted via networks, and used to reconstruct images which can be displayed on monitors and other soft copy displays at any desired location.

Artifacts may be introduced into the generated X-ray image due to various factors in the imaging chain. These factors include non-uniformity in scintillator thickness, variations in read-out electronics, tube flux distribution, and inhomogeneities in the cover material overlaying the scintillator. To correct image artifacts arising from these various factors, a gain calibration process employing a gain compensation map may be performed. Because some of these factors, such as contrast variations and artifacts related to scintillator thickness and cover material inhomogeneities, are strongly dependent on the X-ray spectrum incident on the detector, the gain compensation map may be a function of the x-ray spectrum incident on the detector.

Gain calibration is typically performed during installation or system maintenance. The calibration, if fully accounting for variables in the system, would be based upon a number of conditions or combinations of settings, such as the source settings, radiation filter settings, thickness and composition of attenuating object and so forth, which affect the spectra of the radiation used to produce images. The amount of time available to perform this calibration is typically limited however, and, in the interest of time, the digital detector is typically only calibrated at finite acquisition conditions, typically two in the specific case of digital mammography. One of these finite number of calibration maps is then applied to any image acquired at the diagnostic spectrum of interest during actual use. In addition, the patient or other imaged object provides some finite filtration of the spectra which depends on the thickness and composition of the imaged region. The use of a finite number of gain calibration maps in combination with the wide range of spectra actually present in routine imaging situations often produces visible artifacts, particularly in regard to those factors which vary in a spectrum dependent manner.

These deviations and deficiencies in the gain correction maps are particularly notable or evident when the imaged object or region is flat relative to the detector, such as in mammography systems. In mammography, as well as certain other diagnostic situations, the image area of diagnostic interest extends to the edge of the detector. However, due to non-uniformities at the edge of the detector, gain correction may be compromised near the edge, giving rise to strong spectrum sensitive artifacts at the edge. In particular, there may be a fall off in the thickness of the scintillator material, typically cesium iodide (CsI), which can result in spectrally-sensitive contrast variations or artifacts. In such situations, use of a finite number of gain correction maps, each acquired at discrete operating points, may be inadequate to properly correct the gain near the detector edge due to the variation in scintillator thickness and the spectrally-sensitive nature of these artifacts.

In addition, the spectrum dependent variations in gain may result in otherwise acceptable detectors being rejected during quality assurance when a test image is acquired at a spectrum other than those used for calibration. In particular, detector testing and quality assurance for mammography systems, or for other systems where good performance to the edge of the detector is desired, may reject detectors which are otherwise acceptable in these circumstances. In particular, while such variations may not affect the quality of most images, they may nevertheless cause a residual error after gain correction which is higher than allowed to pass image quality specifications. Moreover, calibration at X-ray spectra different than the quality test or diagnostic spectra may lead to detector failure even though proper gain calibration at those spectra would result in an acceptable detector. Poor detector yields from the manufacturing processes result even though proper calibration would improve such yields. A technique for providing gain correction in a time efficient manner and which allows for the artifact-free flat field imaging for all possible acquisition conditions is therefore desirable.

BRIEF DESCRIPTION OF THE INVENTION

The present technique provides a novel approach to minimizing or eliminating image artifacts resulting from detector specific variations which produce spectrum sensitive gain responses. In particular, variations in the scintillator thickness, particularly around the edge of the detector may produce spectrally sensitive gain responses. In addition, during the deposition of the scintillator, particulates of CsI may be deposited which can also introduce abrupt variations in gain calibration maps that are spectrally dependant. The present technique addresses these spectrum specific non-uniformities to provide gain correction over the entire image, including the image edges and CsI particulates.

In accordance with one aspect of the technique, a method is provided for producing an adapted gain correction map. A gain correction map for a detector derived from a first X-ray spectrum is obtained. The gain correction map is adapted based upon a mathematical model. An input including at least one of an acquisition condition and a detector attribute is provided for the model, and an adapted gain correction map results. The adapted gain correction map corrects gain in an image generated by the detector at a second X-ray spectrum.

In accordance with a further aspect of the technique, a method is provided for producing a gain corrected image. An image is acquired from an X-ray detector from a first X-ray spectrum. A gain correction map, which was derived from a second X-ray spectrum, is applied to the image to produce a gain adapted image. One or more respective correction factors is applied to a plurality of pixels comprising one of an edge row and an edge columns of the gain adapted image to form a gain corrected image.

In accordance with another aspect of the technique, a method is provided for determining gain correction factors for an image edge. An X-ray image is acquired using a detector exposed to an X-ray spectrum and an object of interest. Two or more measures of central tendency of pixel intensity for one of non-edge columns and non-edge rows of the X-ray image is determined. A trend for the measures of central tendency is calculated. one or more correction factors based upon the trend for one of edge columns and edge rows, respectively, of the X-ray image is calculated.

In accordance with a further aspect of the technique, a X-ray system is provided comprising a X-ray source configured to emit a plurality of X-ray spectra and a X-ray detector configured to detect X-rays emitted by the X-ray source. In addition, the system comprises a detector controller operably coupled to the X-ray detector and a system controller, operably coupled to the detector controller. At least one of the detector controller and the system controller are configured to provide at least one of an acquisition condition and a detector attribute to a mathematical model and to generate an adapted gain correction map by applying the mathematical model to a gain correction map acquired from a first X-ray spectrum. The adapted correction map is adapted to correct gain in an image acquired from a second X-ray spectrum.

In accordance with a different aspect of the technique, a X-ray system is provided comprising a X-ray source configured to emit a plurality of X-ray spectra and a X-ray detector configured to detect X-rays emitted by the X-ray source. In addition, the system comprises a detector controller operably coupled to the X-ray detector and a system controller, operably coupled to the detector controller. At least one of the detector controller and the system controller are configured to apply one or more correction factors to a plurality of pixels comprising an edge region of an X-ray image to form a gain corrected image.

In accordance with a further aspect of the technique, a tangible medium for producing an adapted gain correction map is provided comprising a routine for obtaining a gain correction map for a detector derived from a first X-ray spectrum. The tangible medium further comprises a routine for adapting the gain correction map based upon a mathematical model which accepts as an input at least one of an acquisition condition and a detector attribute. An adapted gain correction map results which corrects gain in an image generated by the detector from a second X-ray spectrum.

In accordance with a another aspect of the technique, a tangible medium for producing a gain corrected image is provided comprising a routine for acquiring an image from an X-ray detector from a first X-ray spectrum. The tangible medium further comprises a routine for applying a gain correction map derived from a second X-ray spectrum to the image to produce a gain adjusted image. In addition, the tangible medium comprises a routine for applying one or more respective edge correction factors to a plurality of edge pixels comprising one or more edge of the gain adjusted image to form a gain corrected image.

In accordance with a different aspect of the technique, a X-ray system is provided comprising a X-ray source configured to emit a plurality of X-ray spectra and a X-ray detector configured to detect X-rays emitted by the X-ray source. In addition, the system comprises a detector controller operably coupled to the X-ray detector and a system controller, operably coupled to the detector controller. At least one of the detector controller and the system controller comprise a means for adjusting a gain correction map to form an adjusted gain correction map which corrects gain in an image generated by the detector.

In accordance with a different aspect of the technique, a X-ray system is provided comprising a X-ray source configured to emit a plurality of X-ray spectra and a X-ray detector configured to detect X-rays emitted by the X-ray source. In addition, the system comprises a detector controller operably coupled to the X-ray detector and a system controller, operably coupled to the detector controller. The system also includes a means for correcting gain in an acquired X-ray image based upon at least one of one or more detector attributes, one or more acquisition conditions, and one or more mathematical models.

DETAILED DESCRIPTION OF SPECIFIC EMBODIMENTS

Figure 1:
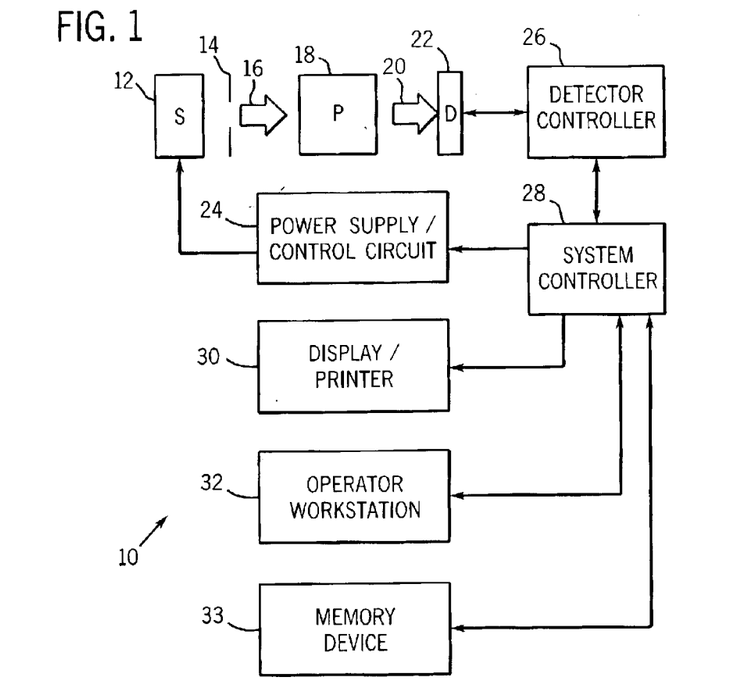
FIG. 1 is a diagrammatical overview of a digital X-ray imaging system in which the present technique is incorporated.

FIG. 1 illustrates diagrammatically an imaging system 10 for acquiring and processing discrete pixel image data. In the illustrated embodiment, system 10 is a digital X-ray system designed both to acquire original image data, and to process the image data for display in accordance with the present technique. In the embodiment illustrated in FIG. 1, imaging system 10 includes a source of X-ray radiation 12 positioned adjacent to a collimator 14. The source 12 includes a target which is bombarded with electrons and, in response produces a stream of radiation 16 consisting of X-ray photons. In addition, the source 12 may include a spectral filter which limits the spectrum of X-ray radiation comprising the stream of radiation 16. In mammography applications, the target may be composed of molybdenum, rhodium or tungsten while the spectral filter may be composed of aluminum, molybdenum or rhodium. The composition of both the target and the spectral filter, as well as the acceleration voltage of the applied electron beam, determine the X-ray spectrum emitted by the source 12. The spectrum may be further modified by the attenuating path through which x-rays traverse.

Collimator 14 permits the stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry 33 for storing programs and routines executed by the computer, as well as configuration parameters and image data, interface circuits, and so forth. The memory circuitry 33 may include various magnetic, optical, or other common storage media.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked to the system for outputting system parameters, requesting examinations, viewing images, and so forth. In general, displays, printers, workstations, memory circuitry and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
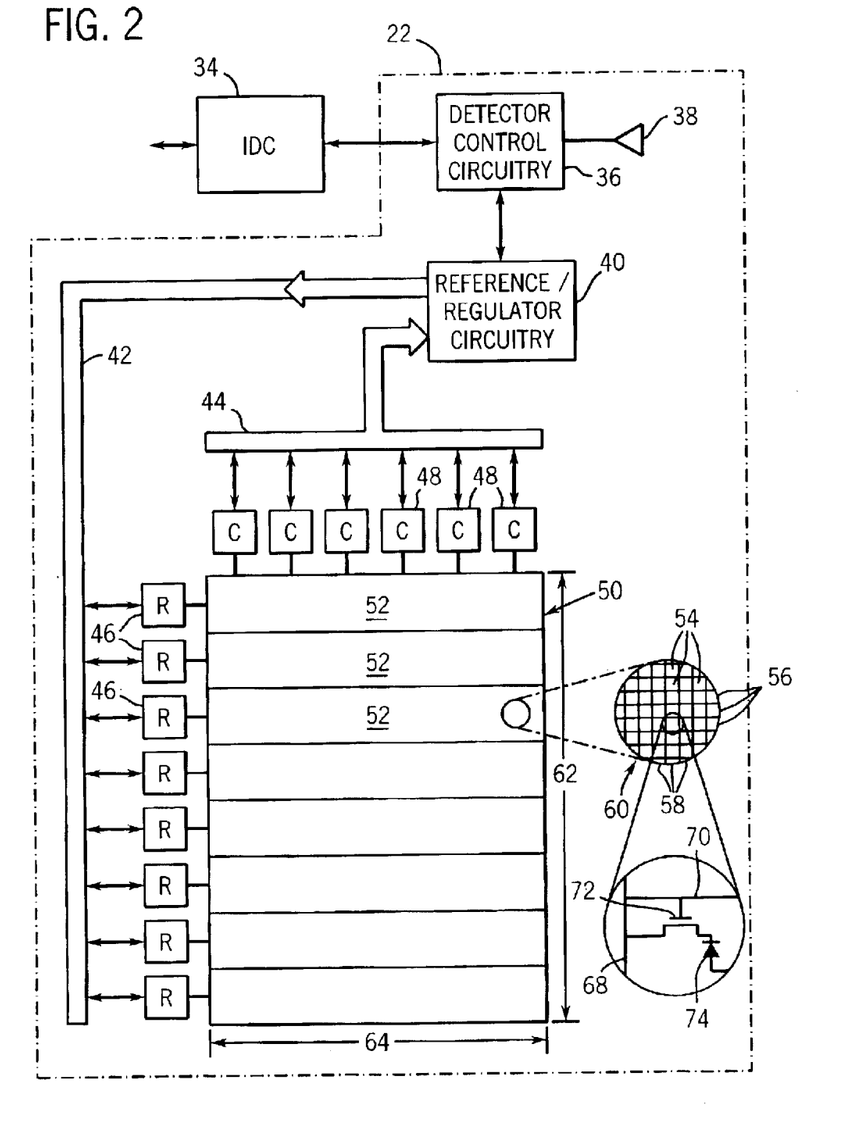
FIG. 2 is a diagrammatical representation of certain of the functional circuitry for producing image data in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation. Memory circuits resident within either the detector 22 or the IDC 34 store data that can be accessed subsequently. For example, the data may be provided to the resident memory circuits during manufacture of the detector 22 and its related circuitry or the data may be downloaded to the memory circuits after manufacture or installation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a presently preferred embodiment illustrated, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
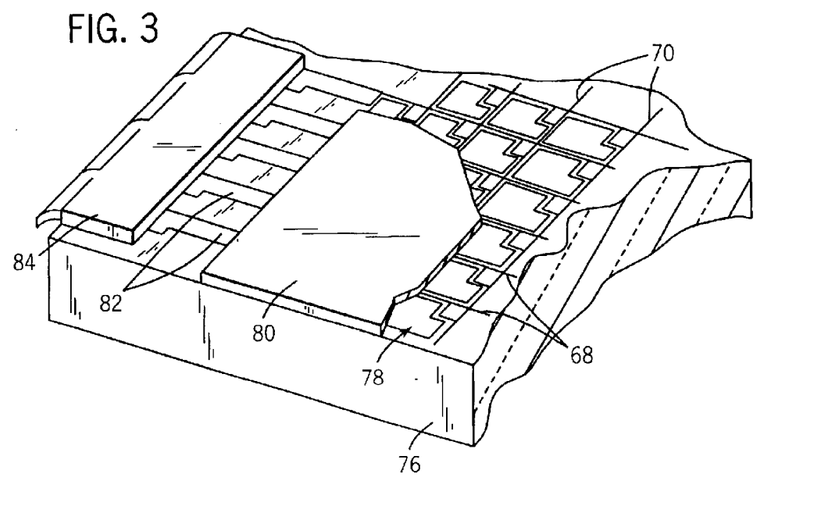
FIG. 3 is a partial sectional view illustrating an exemplary detector structure for producing the image data.

FIG. 3 generally represents an exemplary physical arrangement of the components illustrated diagramatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array 78 for receiving radiation during examination sequences as described above. Contact fingers 82 are formed for communicating signals to and from the column and row electrodes, and contact leads 84 are provided for communicating the signals between the contact fingers and external circuitry.

Figure 4:
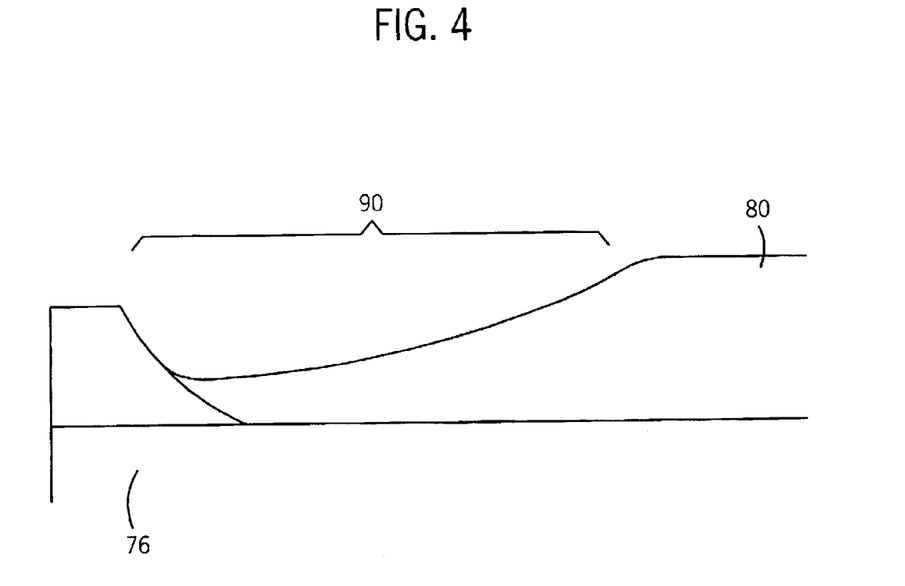
FIG. 4 is a cross-sectional view illustrating the variation in scintillator height which is present near the edge of a detector.

The scintillator 80 is typically formed of cesium iodide (CsI) crystals which are grown on the amorphous silicon array 78 and glass substrate 76 by vapor deposition techniques. Typically, the desired thickness of the CsI layer is 50–350 µm in mammography applications, and can be as high as 700 microns in fluoroscopic or radiographic applications. The deposition process may result in the thickness of the scintillator 80 tapering off as it approaches the edges of the substrate 76, as depicted in FIG. 4. The tapered edge 90 may be of varying thickness and generally terminates at an epoxy dam 92 disposed about the edges of the substrate 76.

The tapered edge 90, and other non-uniformities in the detector or layers thereof, result in a gain response in the detector 22. This gain response varies at different positions on the detector 22, even when the X-ray flux uniformly strikes the detector and is of a given spectrum, because the gain is a function not only of the X-ray spectrum and uniformity, but also of the scintillator 80 thickness. Gain calibration is performed at a particular X-ray spectrum to derive a gain correction map at that spectrum. The gain correction map may then be applied to an image on a pixel-by-pixel basis to correct the gain response as long as the X-ray spectrum during image acquisition is the same as that when gain calibration was performed.

However, if the X-ray spectrum incident on the detector during image acquisition differs from that used during gain calibration, the tapered region 90 and other non-uniformities will generate a gain response which is not properly corrected by the gain calibration map, i.e. the gain correction process leaves residual errors due to the lack of correspondence between the calibration map and the gain variation observed during acquisition. This improperly corrected gain response may manifest itself as variations in image contrast which may be visible as image artifacts. Abrupt variations in CsI thickness in the diagnostic region may produce these residual errors, creating the appearance of an anatomical structure resulting in interpretation errors. In particular, the edge of the detector 22 may be prone to such abrupt variations in CsI thickness due to the deposition process, resulting in image artifacts that may hinder interpretation in mammography and in other applications in which the desired image area extends to the detector edge.

For example, in mammography, for practical reasons, such as the time required to perform a gain calibration, only two gain calibrations are typically performed on an X-ray system 10. In such cases, only two gain correction maps obtained at different X-ray spectra are available for gain correction by the system 10. These gain correction map acquired under conditions most closely corresponding to the actual imaging conditions is therefore applied to an acquired image, regardless of whether the X-ray spectra at image acquisition corresponds exactly to that at gain calibration, producing visible image artifacts at the edge in some instances. In addition, the imaged object, such as a patient's breast, filters the X-ray spectrum by some amount, depending on the thickness of the imaged object and its composition. A technique for performing gain correction when the X-ray spectrum during image acquisition differs from that during gain calibration is therefore desirable to reduce or eliminate spectrally-sensitive artifacts from the acquired image.

Figure 5:
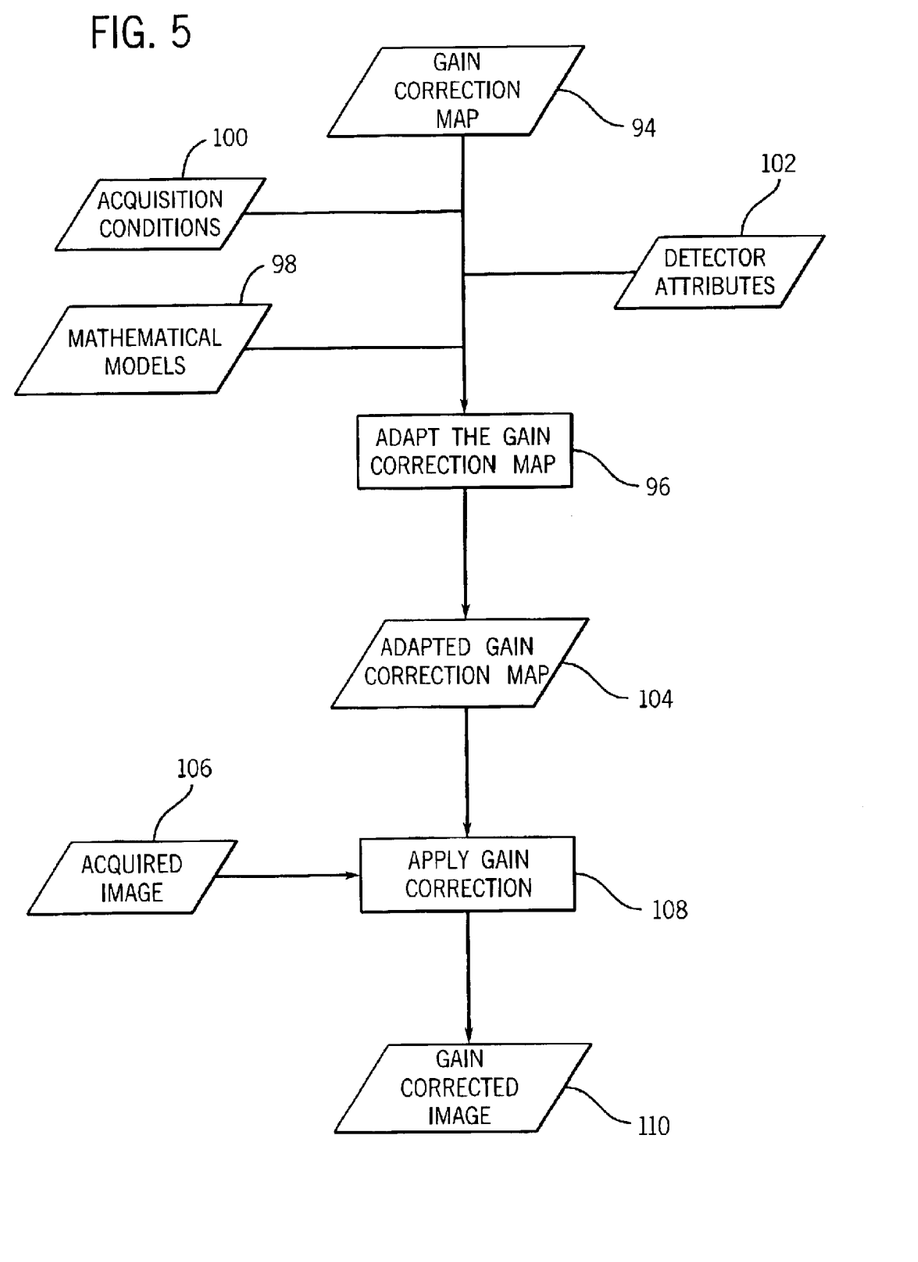
FIG. 5 is a flowchart of one embodiment of the present technique in which an adapted gain correction map is utilized.

In accordance with a present embodiment, as depicted in FIG. 5, a gain correction map 94 is adapted using known factors and models. The gain correction map 94 may be generated by a prior gain calibration step at a first X-ray spectrum. In the event that more than one gain correction map 94 has been pre-generated and is accessible, the gain correction map 94 selected for adaptation may be selected based upon similarity of one or more acquisition conditions 100. For example, the gain correction map 94 may be selected which is derived at acquisition conditions 100, which may include the acceleration voltage applied by the system, the composition of the target, the composition of the spectral filter, the thickness of the spectral filter, the thickness of the attenuating object, the composition of the attenuating object, and other known objects in the attenuation path, that are similar to the current acquisition conditions 100. The step of adaptation 96 utilizes a mathematical model 98 which accounts for factors such as the acquisition conditions 100 or detector attributes 102 to form the adapted gain correction map 104. In practice, the adaptation step 96 is performed by either the system controller 28 or the detector controller 26 of the system 10.

The acquisition conditions 100 noted above generally encompass those factors which determine the actual X-ray spectrum incident upon the detector 22. Similarly the detector attributes 102 generally encompass those factors which determine the varying spectrum sensitivity of the detector 22, and may include variations in scintillator thickness, the composition of any protective cover material overlying the scintillator, and inhomogeneities in the protective cover material. The detector attributes 102 can be collected during manufacture of the detector 22 or may be determined through a separate calibration process. The detector attributes 102 may be stored on the system 10, such as in a memory resident on the detector 22 or detector controller 26, or on a medium accessible to the system 10, in a computer-readable format, such as data code stored on a magnetic, optical or network accessible medium.

The mathematical model 98 accounts for the factors comprising the acquisition conditions 100 and the detector attributes 102 such that, when these factors are provided to the model during the adaptation step 96, an adapted gain correction map 104 is formed for detector 22 which properly corrects for gain at the actual imaging spectrum. The mathematical model 98 may be empirically or theoretically derived based upon known relationships between the factors determining X-ray spectrum, scintillator thickness, or any other arbitrary acquisition conditions. In this manner, an adapted gain correction map 104 may be produced which provides proper gain correction for the detector 22 at the acquisition X-ray spectrum, not simply at the calibration spectra. The adapted gain correction map 104 may then be applied to an image 106 acquired under the acquisition conditions, as depicted at step 108, to produce a gain corrected image 110. As with the detector attributes 102, the mathematical models 98 may be stored in a computer readable form on the system 10 itself or on an accessible medium.

The mathematical model may also be run a-priori for a number of acquisition conditions, such as those acquisition conditions most commonly employed in the field, and the results storied on the system 10 or on an accessible medium. If a corresponding mathematical model has been run a-priori and the result is accessible to the system, it is not necessary to calculate the mathematical model on the fly.

Figure 6:
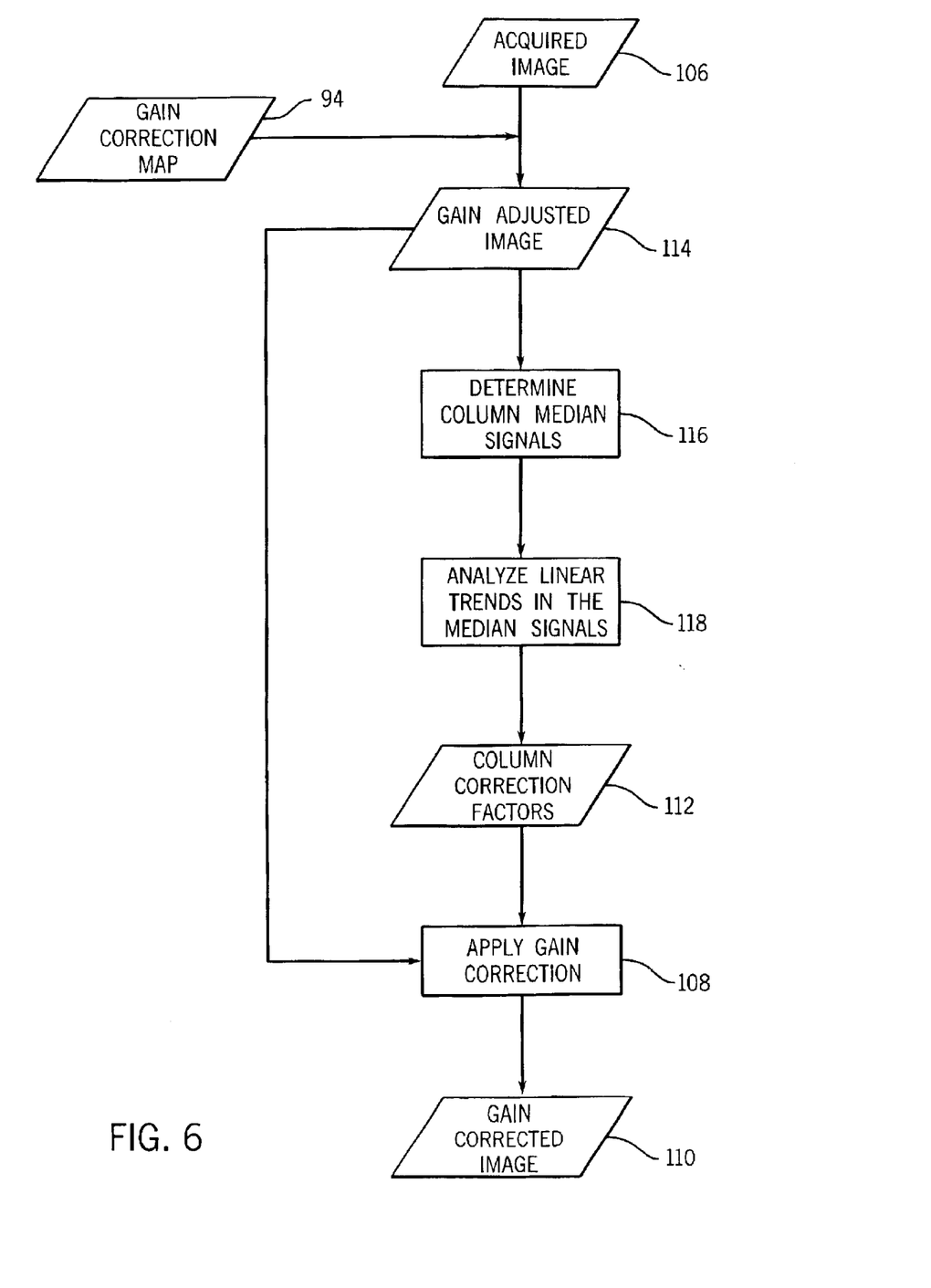
FIG. 6 is a flowchart of another embodiment of the present technique in which column correction factors are derived.

An alternative technique for correcting spectrally-sensitive artifacts due to scintillator thickness variations uses the acquired image 106, as depicted in FIG. 6, to correct known trends at the edge of the detector 22. In particular, correction factors 112 corresponding to the columns or rows near the edge of the detector 22 are calculated using information from other columns 58 or rows 56 in the acquired image. For purposes of illustration, calculation of a column correction factor 112 is depicted in FIG. 6 for edge columns, though it is to understood that the depicted process is also applicable to edge rows.

Initially, the acquired image 106 is nominally corrected using a gain correction map 94 resident on the system 10 to produce a gain adjusted image 114. The median signal intensity within columns parallel to the edge is then determined at step 116 for the gain adjusted image 114. Trends, typically linear in nature, in the column median signal intensity are then analyzed at step 118 to derive gain correction factors 112 for each column near the edge of the detector 22. Derivation of these gain correction factors 112 may be accomplished by a line-fitting algorithm or by various other mathematical fit criteria. The derived gain correction factors 112 are then applied to the gain adjusted image 114 at step 108 to produce the gain corrected image 110. Though the median signal intensity within columns or rows is discussed, any measure of central tendency, such as means or modes, may be utilized and the use of a median is only one possibility.

In one embodiment, the detector attributes, such as CSI thickness at each pixel, are estimated during the detector 22 manufacturing process. These detector attributes can then be used to adapt the gain calibration map 94 by a spectrally-sensitive factor. A look-up-table accessible by the system controller 28 or the detector controller 26 can store the detector attributes or a predetermined adaptation appropriate for the acquisition operating space. The look-up table may be stored in a memory medium, such as flash memory, on the system 10, such as on the detector 22 or detector controller 26, or may be stored on some other magnetic, optical, or network-accessible media. From this stored location, the system 10 may access the detector attributes and derive or apply the appropriate gain correction map 94 for the acquisition conditions, to an acquired image 106 to produce a gain adjusted image 114 for further processing, as depicted in FIG. 6.

While the invention may be susceptible to various modifications and alternative forms, specific embodiments have been shown by way of example in the drawings and have been described in detail herein. However, it should be understood that the invention is not intended to be limited to the particular forms disclosed, including the specific application to digital mammographic imaging. Rather, the invention is to cover all modifications, equivalents, and alternatives falling within the spirit and scope of the invention as defined by the following appended claims.

What is claimed is:

1. A method for producing an adapted gain correction map, comprising:
    obtaining a gain correction map for a detector derived from a first X-ray spectrum; and
    adapting the gain correction map based upon a mathematical model, wherein the mathematical model is provided an input of at least one of an acquisition condition and a detector attribute, such that an adapted gain correction map results wherein the adapted gain correction map corrects gain in an image generated by the detector at a second X-ray spectrum.

2. The method as recited in claim 1, wherein adapting the gain correction map includes providing one or more acquisition conditions comprising at least one of an acceleration voltage applied to a target in an X-ray source, a composition of the target, a composition of a spectral filter associated with the X-ray source, a thickness of the spectral filter, a thickness of an attenuating object, and a composition of the attenuating object.

3. The method as recited in claim 1, wherein adapting the gain correction map includes providing one or more detector attributes comprising at least one of a composition of a protective cover overlying a scintillator associated with the detector, one or more inhomogeneities in the protective cover, and one or more variations in the scintillator thickness.

4. The method as recited in claim 3, further comprising accessing a memory location in which the one or more detector attributes are stored.

5. The method as recited in claim 4, wherein accessing the memory location comprises accessing at least one of a magnetic medium and an optical medium.

6. The method as recited in claim 4, wherein accessing the memory location comprises accessing at least one of a network accessible memory location and a resident memory location.

7. The method as recited in claim 6, wherein the resident memory location is located on the detector.

8. The method as recited in claim 1, wherein obtaining the gain correction map comprises selecting the gain correction map from two or more available gain correction maps based upon at least one of an acceleration voltage applied to a target in an X-ray source, a composition of the target, a composition of a spectral filter associated with the X-ray source, a thickness of the spectral filter, a thickness of an attenuating object, and a composition of the attenuating object.

9. The method as recited in claim 1, further comprising applying the adapted gain correction map to an image acquired at the second X-ray spectrum to produce a gain corrected image.

10. A method for producing a gain corrected image, comprising:
    acquiring an image from an X-ray detector from a first X-ray spectrum;
    applying a gain correction map to the image to produce a gain adapted image, wherein the gain correction map was derived from a second X-ray spectrum; and
    applying one or more respective correction factors to a plurality of pixels comprising one of edge rows and edge columns of the gain adapted image to form a gain corrected image.

11. The method as recited in claim 10, further comprising:
    determining a measure of central tendency of pixel intensity of each of two or more non-edge columns of the gain adapted image;
    calculating a linear trend for the two or more measures of central tendency; and
    calculating the respective column correction factor for each of one or more edge columns based upon the linear trend.

12. The method as recited in claim 11, wherein determining the measure of central tendency comprises determining one of a median, a mean, and a mode.

13. The method as recited in claim 10, further comprising:
    determining a measure of central tendency of pixel intensity of each of two or more non-edge rows of the gain adapted image;
    calculating a linear trend for the two or more measures of central tendency; and
    calculating the respective row correction factor for each of one or more edge rows based upon the linear trend.

14. The method as recited in claim 13, wherein determining the measure of central tendency comprises determining one of a median, a mean, and a mode.

15. A method for determining gain correction factors for an image edge, comprising:
    acquiring an X-ray image using a detector exposed to an X-ray spectrum and a an object of interest;

determining a two or more measures of central tendency of pixel intensity for one of non-edge columns and non-edge rows of the X-ray image;

calculating a trend for the measures of central tendency; and calculating one or more correction factors based upon the trend for one of edge columns and edge rows, respectively, of the X-ray image.

16. The method of claim 15, determining the measure of central tendency comprises determining one of a median, a mean, and a mode.

17. A X-ray imaging system, comprising:

a X-ray source configured to emit a plurality of X-ray spectra;

a X-ray detector configured to detect X-rays emitted by the X-ray source;

a detector controller operably coupled to the X-ray detector; and a system controller, operably coupled to the detector controller;

wherein at least one of the detector controller and the system controller are configured to provide at least one of an acquisition condition and a detector attribute to a mathematical model and to generate an adapted gain correction map by applying the mathematical model to a gain correction map acquired from a first X-ray spectrum, wherein the adapted correction map corrects gain in an image acquired from a second X-ray spectrum.

18. The X-ray imaging system of claim 17, wherein the acquisition condition comprises at least one of an acceleration voltage applied to a target in the X-ray source, a composition of the target, a composition of a spectral filter associated with the X-ray source, a thickness of the spectral filter, a thickness of an attenuating object, and a composition of the attenuating object.

19. The X-ray imaging system of claim 17, wherein the detector attribute comprises at least one of a composition of a protective cover overlying a scintillator associated with the detector, one or more inhomogeneities in the protective cover, and one or more variations in the scintillator thickness.

20. The X-ray imaging system of claim 17, further comprising a computer readable medium upon which at least one of the detector attributes and the mathematical model are stored.

21. The X-ray imaging system of claim 20, wherein the computer readable medium is accessible over a network connection.

22. The X-ray imaging system of claim 20, wherein the computer readable medium comprises at least one of a magnetic medium and an optical medium.

23. A computer-readable medium for producing an adapted gain correction map, comprising:

a routine for obtaining a gain correction map for a detector derived from a first X-ray spectrum; and a routine for adapting the gain correction map based upon a mathematical model, wherein the mathematical model accepts as an input at least one of an acquisition condition and a detector attribute, such that an adapted gain correction map results wherein the adapted gain correction map corrects gain in an image generated by the detector from a second X-ray spectrum.

24. The computer-readable medium of claim 23, wherein the routine for adapting the gain correction map provides for inputting one or more acquisition conditions comprising at least one of an acceleration voltage applied to a target in an X-ray source, a composition of the target, a composition of a spectral filter associated with the X-ray source, a thickness of the spectral filter, a thickness of an attenuating object, and a composition of the attenuating object.

25. The computer-readable medium of claim 23, wherein the routine for adapting the gain correction map provides for inputting one or more detector attribute comprising at least one of a composition of a protective cover overlying a scintillator associated with the detector, one or more inhomogeneities in the protective cover, and one or more variations in the scintillator thickness.

26. The computer-readable medium of claim 25, further comprising a routine for accessing a memory location in which the one or more detector attributes are stored.

27. The computer-readable medium as recited in claim 26, wherein accessing the memory location comprises accessing at least one of a magnetic medium and an optical medium.

28. The computer-readable medium as recited in claim 26, wherein accessing the memory location comprises accessing at least one of a network accessible memory location and a resident memory location.

29. The computer-readable medium of claim 23, further comprising a routine for applying the adapted gain correction map to an image acquired at the second X-ray spectrum to produce a gain corrected image.

30. The computer-readable medium of claim 23, wherein the routine for obtaining a gain correction map selects the gain correction map from two or more available gain correction maps based upon at least one of an acceleration voltage applied to a target in an X-ray source, a composition of the target, a composition of a spectral filter associated with the X-ray source, a thickness of the spectral filter, a thickness of an attenuating object, and a composition of the attenuating object.

31. A computer-readable medium for producing a gain corrected image, comprising:

a routine for acquiring an image from an X-ray detector from a first X-ray spectrum;

a routine for applying a gain correction map to the image to produce a gain adapted image, wherein the gain correction map was derived from a second X-ray spectrum; and a routine for applying one or more respective edge correction factors to a plurality of edge pixels comprising one or more edges of the gain adapted image to form a gain corrected image.

32. The computer-readable medium of claim 31, further comprising:

a routine for determining two or more measures of central tendency of pixel intensity for one of columns and rows of the gain adapted image;

a routine for calculating a linear trend for the two or more measures of central tendency; and a routine for calculating the one or more respective correction factors for one of edge columns and edge rows, respectively, based upon the linear trend.

33. The computer-readable medium of claim 32, wherein the routine for determining a measure of central tendency determines one of a median, a mean, and a mode.

34. A X-ray imaging system comprising:

means for obtaining a gain correction map for a detector derived from a first X-ray spectrum: and means for adapting the gain correction map based upon a mathematical model, wherein the mathematical model is provided an input of at least one of an acquisition condition and a detector attribute, such that an adapted gain correction map results wherein the adapted gain correction map corrects cain in an image generated by the detector at a second X-ray spectrum.

* * * * *